United States Patent [19]

Kim et al.

[11] Patent Number: 4,933,465
[45] Date of Patent: Jun. 12, 1990

[54] SILVER HALIDE COLOR PHOTOGRAPHIC MATERIAL

[75] Inventors: Kwang-tae Kim; Young-soo Kim; Jin-youl Kim, all of Kyounggi-do, Rep. of Korea

[73] Assignee: Cheil Synthetic Textile Co., Ltd., Kyoung-Buk, Rep. of Korea

[21] Appl. No.: 292,536

[22] Filed: Dec. 30, 1988

[51] Int. Cl.$^5$ .............................. C07D 231/52
[52] U.S. Cl. ................................ 548/360; 430/386
[58] Field of Search .......................... 548/360

[56] References Cited
U.S. PATENT DOCUMENTS
3,812,145  5/1974  Sato et al. ................. 548/360

Primary Examiner—Robert W. Ramsuer
Attorney, Agent, or Firm—Birch, Stewart, Kolasch & Birch

[57] ABSTRACT

A magenta color - forming coupler represented by the formula (1) for use in color photographic silver halide photosensitive material:

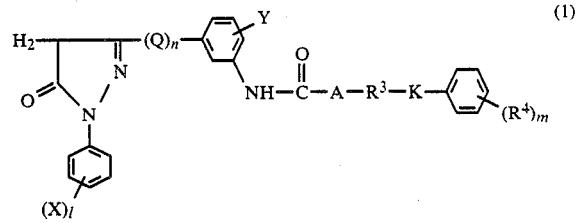

wherein X is halogen; l is 0, 1, 2, or 3; Y is hydrogen or halogen; Q is —NH— or —NHCO—; n is 1, 2, or 3; K is O, S, or SO$_2$; A is

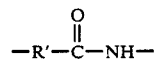

or

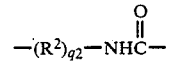

in which R$^1$ represents C$_1$-C$_8$ alkylene or phenylene, R$^2$ represents C$_1$-C$_4$ alkylene or phenylene and q is 1, 2, or 3; R$^3$ is C$_1$-C$_8$ alkylene; R$^4$ is C$_1$-C$_8$ alkyl; and m is an integer of 0, 1, or 2, provided that a plurality of R$^4$ are the same or different each other when m is 2, and a photographic photosensitive material containing the magenta coupler above.

1 Claim, 4 Drawing Sheets

SILVER HALIDE COLOR PHOTOGRAPHIC MATERIAL

BACKGROUND AND FIELD OF THE INVENTION

The present invention relates to a color photographic silver halide photosensitive material, and, more particularly, relates to a magenta coupler for use in a green-sensitive emulsion layer and a process for preparing the same.

In general, a conventional printing paper for color photograph is comprised of 6 to 7 emulsion layers: red-sensitive emulsion layer, green-sensitive emulsion layer and blue-sensitive emulsion layer, including protective emulsion layer, including protective and intermediate layers.

In these layers of the printing paper, the layers which make color images are red-, green- and blue-sensitive. And the structure of each coupler used in the three layers has an great effect on reproduction of color, quality of color images, and reactivity and stability during developing step.

Generally, absorption in the visible portion of the electromagnetic spectrum extends from 400 nm to 700 nm of wavelengths. The human eye has sensors that can detect radiation in the blue, green, and red regions of the visible spectrum, that is, from 400 to 500 nm, 500 to 600 nm, and 600 to 700 nm, respectively. But can not see the separated visible light.

OBJECTS AND SUMMARY OF THE INVENTION

Accordingly, it is an object of the present invention to provide a novel magenta coupler, that is a green-sensitive color-forming agent, having 500 to 600 nm of the visible portion in the electromagnetic spectrum, for use in color photograph.

Another object of the present invention is to provide a novel magenta coupler which makes magenta images having excellent color tone and fastness.

A further object of the present invention is to provide a improved color photograph material without fog during storage which has high color-forming density, excellent reproduction, high sensitivity and high weather resistance.

Other objects and further scope of applicability of the present invention will become apparent from the detailed description given hereinafter. It should be understood, however, that the detailed description and specific examples, while indicating preferred embodiments of the invention are given by way of illustration only, since various changes and modifications within the spirit and scope of the invention will become apparent to those skilled in the art from this detailed description.

The present invention relates to a compound of the formula (1):

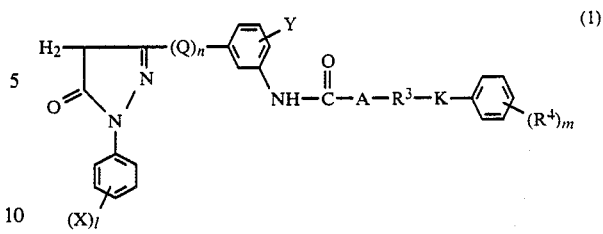

wherein X is halogen; l is 0, 1, 2, or 3; Y is hydrogen or halogen; Q is —NH— or —NHCO—; n is 1, 2, or 3; K is O, S, or $SO_2$; A is

or

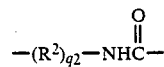

in which $R^1$ represents $C_1$-$C_8$ alkylene or phenylene, $R^2$ represents $C_1$-$C_4$ alkylene or phenylene and q is 1, 2, or 3; is $C_1$-$C_8$ alkylene; $R^4$ is $C_1$-$C_8$ alkyl; and m is an integer of 0, 1, or 2, provided that a plurality of $R^4$ are the same or different each other when m is 2.

DESCRIPTION OF THE PREFERRED EMBODIMENTS

The process for producing the magenta coupler of the present invention comprises reacting a compound of the formula (2):

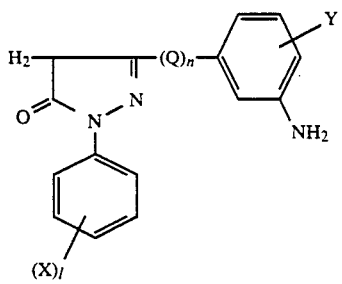

(2)

wherein X is halogen ; l is 0, 1, or 3: Y is hydrogen or halogen; Q is —NH— or —NHCO—; and n is 1, 2 or 3, with a compound of the formula (3):

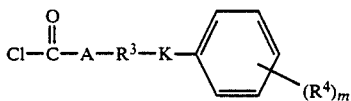

(3)

wherein A is —$R^1$—CONH— or —$(R^2)_q$—NHCO— in which $R^1$ represents $C_1$-$C_8$ alkylene or phenylene, $R^2$ represents $C_1$-$C_4$ alkylene or phenylene and q is 1, 2 or 3; $R^3$ is $C_1$-$C_8$ alkylene; $R^4$ is $C_1$-$C_8$ alkool; K is O, S or $SO_2$; and $m_4$ is an integer of 0,1 or 2, provided that a plurality of $R^4$ are the same or different each other when m is 2.

In the formula (1) and (2) described above, "Y" plays an important role in determing color of the coupler represented by the formula (1) and adjusting the region of the absorption spectrum of the coupler represented by the formula (1), when the formula (1) is synthesized by the reaction of the formula (2) with the formula (3).

The ballasting group represented by the formula (3) is a hydrocarbon comprised of about 10 to 30 of carbon. This ballasting group has an effect on improving diffusibity and solubility of the magenta coupler synthesized in the present invention.

The ballasting group (3) used in the present invention can be prepared as follows:

(1) When "A" in the formula (3) above represents —$R^1$—CONH— wherein $R^1$ is as defined above:

A dicarboxylic acid of the formula (4),

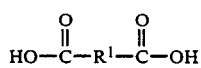

(4)

in which $R^1$ is as defined above, is reacted with thionylchloride ($SOCl_2$) to prepare a compound of the formula (5),

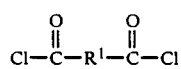

(5)

in which $R^1$ is as defined above, and the resulting diacid chloride of the formula (5) is reacted with the formula (6),

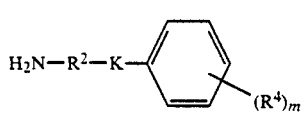

(6)

in which $R^2$, K, $R^4$ and m are as defined above, to prepare one of the ballasting group represented by the formula (3-1),

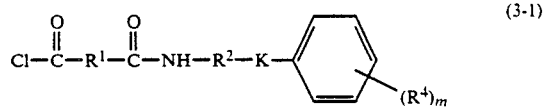

(3-1)

in which $R^1$, $R^2$, K, $R^4$ and m are as defined above.

(2) When "A" in the formula (3) above represents —$(R^2)_q$—NHCO— wherein $R^2$ and q are as defined above:

A compound of the formula (7),

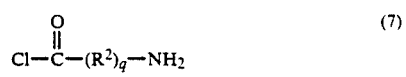

(7)

in which $R^2$ and q are as defined above, is reacted with the formula (8),

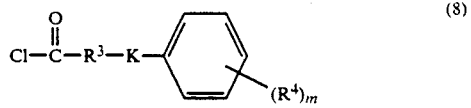

(8)

in which $R^3$, K, $R^4$ and m are as defined above, to prepare the other of the ballasting group represented by the formula (3 - 2 ),

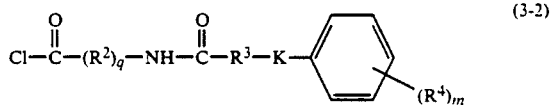

(3-2)

in which $R^2$, q, $R^3$, K, $R^4$ and m are as defined above.

The present invention also relates to a color photographic silver halide photosensitive agent containing about 0.1 to 2 moles of the green-sensitive color-forming agent of the formula (1) per 1 mole of silver halide, and relates to a color photographic photosensitive emulsion coating having average particle size of about 0.3 to 0.8 μm and containing mixed particle of AgCl and AgBr.

Figure 1:
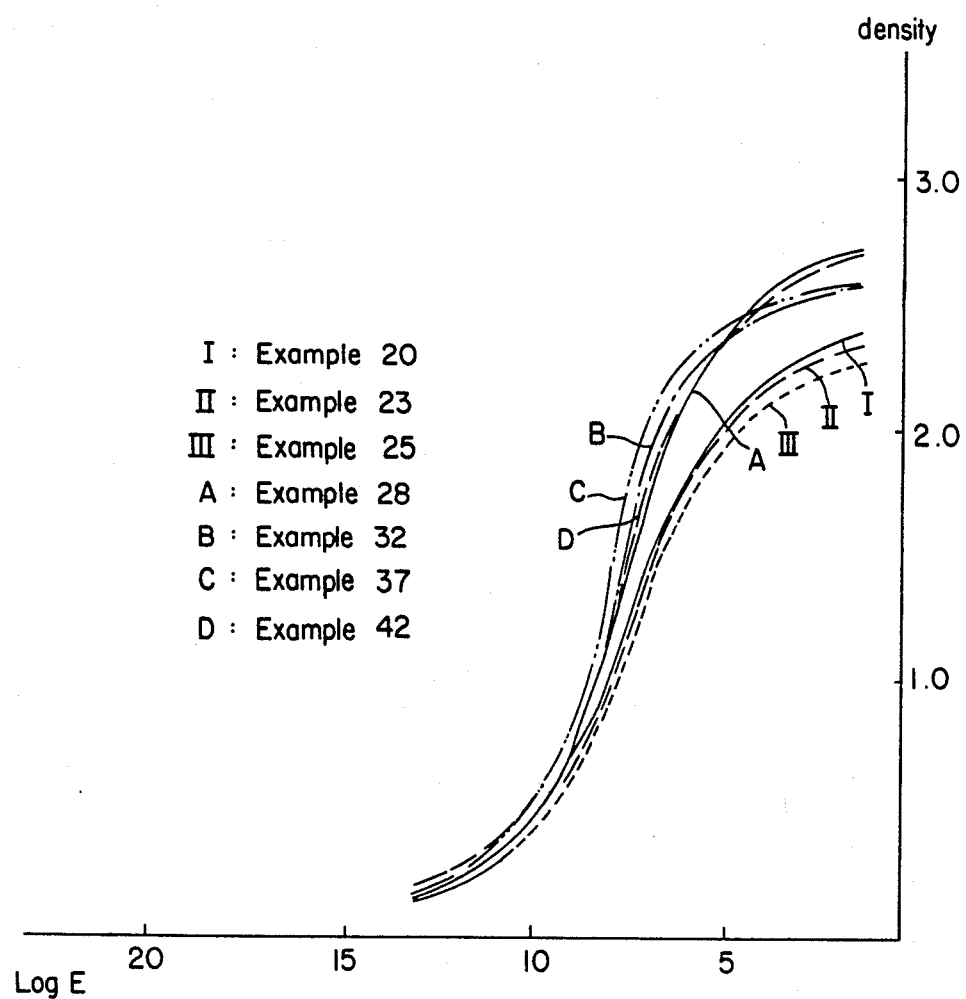
FIG. 1 is a series of magenta characteristic curves which are measured after six-layer coating of the photographic material containing a magenta coupler of the present invention on RC support and exposing the printing paper.
Figure 2:
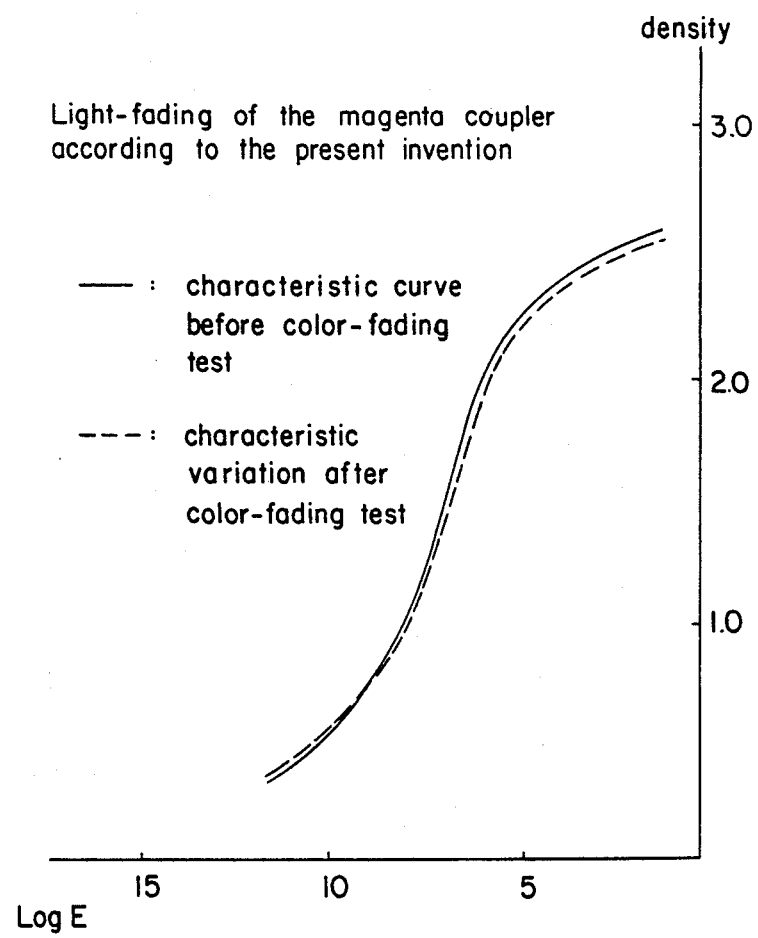
FIG. 2 is characteristic curves showing the result of conditions test of the printing paper after 8 hours under conditions of 538 Lux of illumination, 60° C.±3 of temperature and 50% of relative humidity, which is coated with the photographic material containing a magenta coupler of the present invention.
Figure 3:
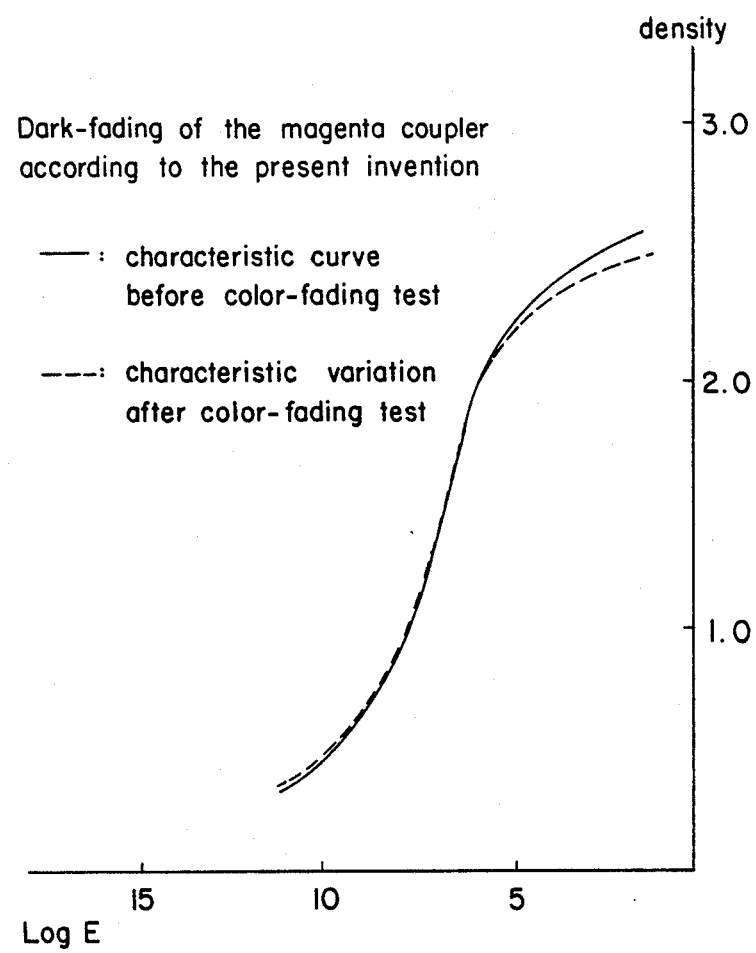
FIG. 3 is characteristic curves showing the result of color-fading test of the printing paper after 48 hours under conditions of 538 Lux of illumination, 60 °C. ±3 of temperature and 50% of relative humidity, which is coated with the photographic material containing a magenta coupler of the present invention.
Figure 4:
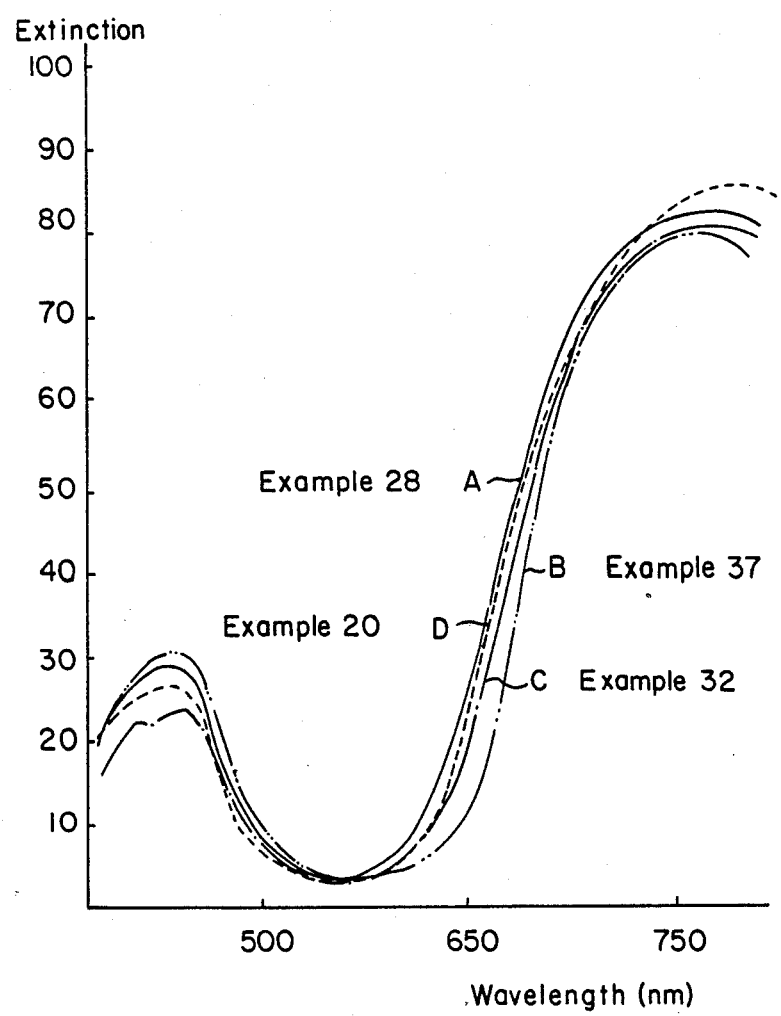
FIG. 4 is a series of absorption spectrum curves of magenta couplers of the present invention and conventional magenta coupler.

In FIG. 1 are shown a series of characteristic curves of the color photography measured after coating various photosensitive emulsions on the resin-coating printing paper, and in FIG. 4 are shown a series of absorption wavelength curves of various magenta couplers of the present invention including conventional magenta couplers. FIG. 2 and FIG. 3 are curves illustrating light-fading and dark-fading of the magenta coupler prepared in the present invention, respectively.

The green-sensitive couplers of the present invention have excellent fastness, stability and high-temperature resistance as well as have 500 to 600 nm of absorption wavelength which appear in case of magent coupler during developing (see FIG. 4).

The present invention will now be described in more detail in connection with the following examples which should be considered as being exemplary and not limiting of the present invention.

EXAMPLE 1-6

These examples illustrate the synthesis of compound (8) described above:

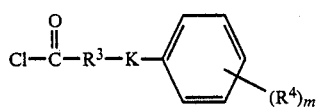   (8)

wherein $R^3$ is $C_1$–$C_8$ alkylene, $R^4$ is $C_1$–$C_8$ alkylene, K represents O, S, or $SO_2$, and m is an integer of 0,1 or 2 provided that a plurality of $R^4$ are the same or different each other when m is 2.

EXAMPLE 1

Synthesis of 2-(2,4-di-tert-pentylphenoxy) butylyl chloride

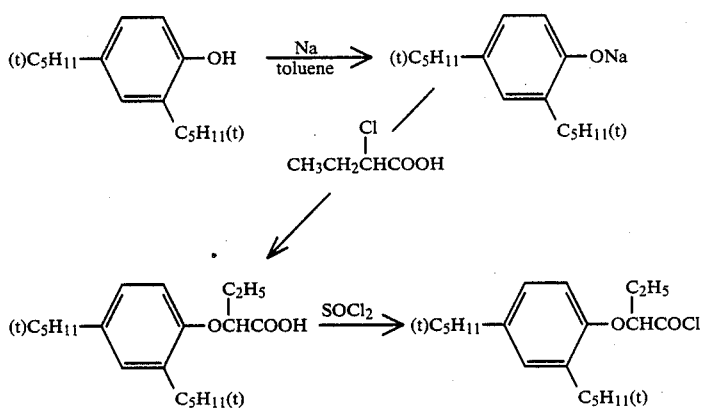

In 300 ml of toluene, 1 mole of 2,4-di-tert-amylphenol is reacted with 23 g of sodium to prepare sodium salt of 2,4-di-tert-amylphenol, and then 1 mole of 2-chlorobutylic acid is added to the reaction product to synthesize 2-(2,4-di-amylphenoxy)butylic acid.

After the solvent is removed under reduced pressure, said 2-(2,4-di-amylphenoxy)butylic acid is resolved in 500 ml of tetrachlorocarbon, 0.12 mole of thionylchloride is dropped slowly to the solution, and the reaction solution is stirred at 60° to 80° C. for 5 to 10 hours.

The resultant product is obtained with yield of 90 to 95% after distil off $CCl_4$ under reduced pressure.

The thus obtained product is identified by ultrared spectrometer and NMR spectrometer.

The specific peaks appears at 1800 cm$^{-1}$ and 2960 cm$^{-1}$ when analyze with ultrared spectrometer.

EXAMPLE 2

Synthesis of 4-(4-pentylphenoxy)butylyl chloride

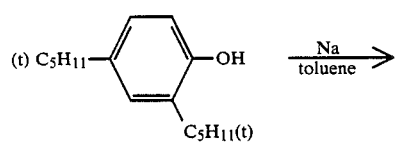

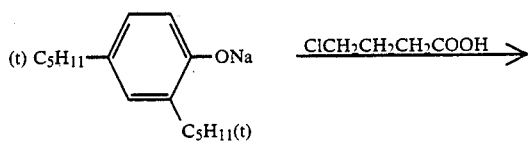

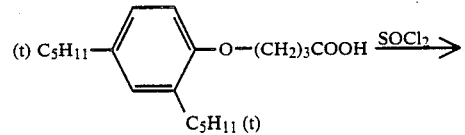

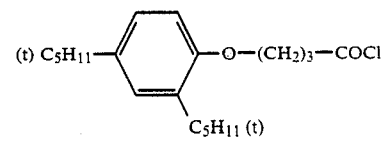

4-(4-pentylphenoxy)butylyl chloride is obtained using 1 mole of 4-chlorobutylic acid instead of 2-chlorobutylic acid in example 1.

Various compounds (8) prepared by the method described in example 1 are shown in Table 1.

TABLE 1

| Examples | Compounds | Yield | Color |
|---|---|---|---|
| 1 | (t)C$_5$H$_{11}$—⌬—OCHCOCl (C$_2$H$_5$), C$_5$H$_{11}$(t) | 85% | Yellow |
| 2 | (t)C$_5$H$_{11}$—⌬—OCH$_2$CH$_2$CH$_2$COCl, C$_5$H$_{11}$(t) | 86% | " |
| 3 | (t)C$_5$H$_{11}$—⌬—OCH$_2$COCl | 87% | " |
| 4 | (t)C$_5$H$_{11}$—⌬—OCH$_2$COCl, C$_5$H$_{11}$(t) | 85 | " |

TABLE 1-continued

| Examples | Compounds | Yield | Color |
|---|---|---|---|
| 5 | (n)C8H11—⟨ ⟩—OCH2CH2CH2COCl | 80% | " |
| 6 | (t)C5H11—⟨ ⟩—O(CH2)4COCl, C5H11(t) | 78% | " |

EXAMPLE 7-12

These examples illustrate the synthesis of compound (3-1) wherein A is —R$^1$—CO—NH— in which R$^1$ represents C$_1$-C$_8$ alkylene or benzyl:

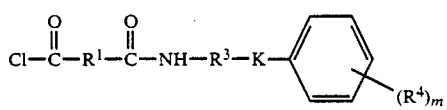

wherein R$^3$ is C$_1$-C$_8$ alkylene, R$^4$ is C$_1$-C$_8$ alkylene, K represents O, S or SO$_2$, and m is an integer of 0, 1, or 2 provided that a plurality of R$^4$ are same or different each other when m is 2.

EXAMPLE 7

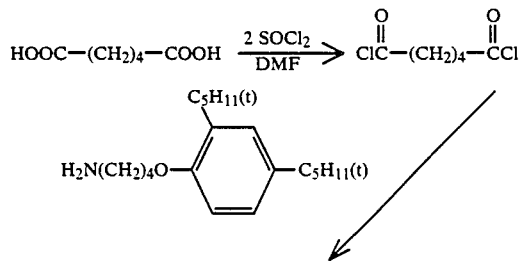

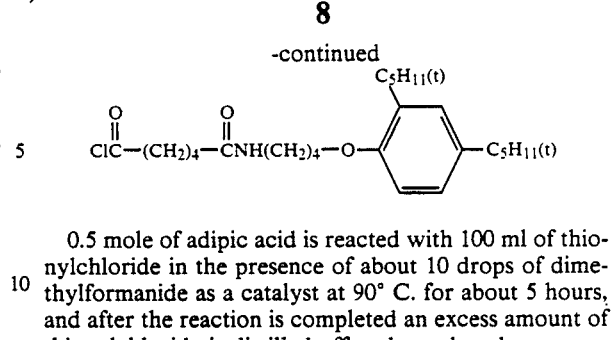

0.5 mole of adipic acid is reacted with 100 ml of thionylchloride in the presence of about 10 drops of dimethylformanide as a catalyst at 90° C. for about 5 hours, and after the reaction is completed an excess amount of thionylchloride is distilled off under reduced pressure.

The thus resultant dichloroadipic acid is diluted with 200 ml of chloroform and the reaction solution is reacted with 0.5 mole of 4-(2,4-di-tert-phenylphenoxy) butylamine at 60° to 80° C.

After the reaction is completed the solvent used herein is distilled off and the titled reaction product is obtained.

The reaction product is confirmed by ultrared spectrometer and NMR spectrometer.

EXAMPLE 8

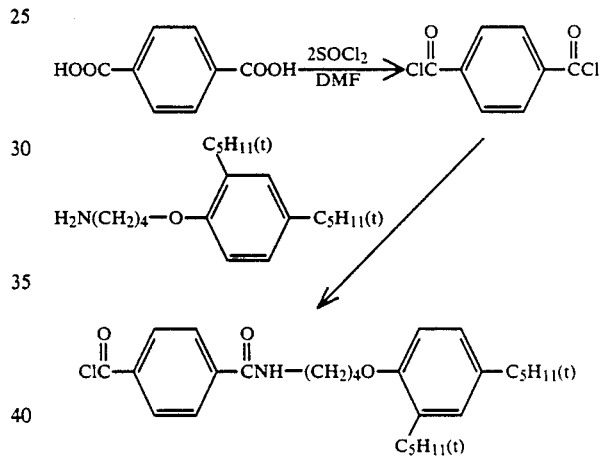

The titled reaction product is obtained using 0.5 mole of terephthalic acid instead of adipic acid in Example 7.

Various compounds (3-1) prepared by the method described in Example 7 are shown in Table 2.

TABLE 2

| Examples | Compounds | Yield | Color |
|---|---|---|---|
| 7 | (t)C5H11—⟨ ⟩—O(CH2)4NHC(CH2)2CCl, C5H11(t) | 90% | Yellow |
| 8 | (t)C5H11—⟨ ⟩—O(CH2)4NHC—⟨ ⟩—CCl, C5H11(t) | 92% | " |
| 9 | (t)C5H11—⟨ ⟩—O(CH2)4NHC(CH2)4CCl, C5H11(t) | 88% | " |

TABLE 2-continued

| Examples | Compounds | Yield | Color |
|---|---|---|---|
| 10 | (t)C$_5$H$_{11}$—⟨benzene with C$_5$H$_{11}$(t)⟩—O(CH$_2$)$_4$NHCCH=CHCCl (with two C=O) | 88% | " |
| 11 | (t)C$_5$H$_{11}$—⟨benzene with C$_5$H$_{11}$(t)⟩—O(CH$_2$)$_4$NHC(O)—⟨benzene⟩—C(O)—Cl | 85% | " |
| 12 | (t)C$_5$H$_{11}$—⟨benzene with C$_5$H$_{11}$(t)⟩—O(CH$_2$)$_4$NHC(O)(CH$_2$)$_8$C(O)Cl | 86% | " |

EXAMPLE 13-18

These examples illustrate the synthesis of compound (3-2) wherein A is —(R$^2$)$_q$—NHCO— in which R$^2$ represents C$_1$—C$_4$ alkylene or benzyl, and q is 1, 2 or 3:

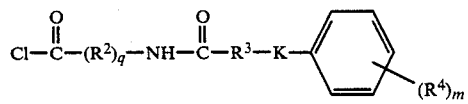

wherein R$^3$ is C$_1$–C$_8$ alkylene, K is O, S or SO$_2$, R$^4$ is C$_1$–C$_8$ alkylene and, m is an integer of 0.1 0, 1 or 2 provided that a plurality of R$^4$ are same or different each other when m is 2.

EXAMPLE 13

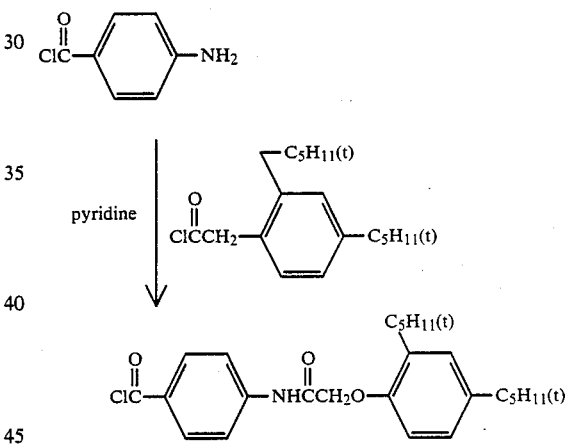

To a solution of 4-aminobenzoylchloride(0.1 mole) in pyridine (300 ml) is added 0.1 mole of (2,4-di-amyl-phenoxy) acetyl chloride and the reaction is carried out with agitation at 60° to 70° C. for 6 to 8 hours.

After completion of the reaction 200 ml of n-hexane is added to remove the pyridine as a form of pyridine salt and and the titled reaction product is obtained.

The reaction product is confirmed by ultrared spectrometer and NMR spectrometer.

Various compounds (3-2) prepared by the method, described in Example 13 are shown in Table 3.

TABLE 3

| Examples | Compounds | Yield | Color |
|---|---|---|---|
| 13 | (t)C$_5$H$_{11}$—⟨benzene with C$_5$H$_{11}$(t)⟩—OCH$_2$C(O)NH—⟨benzene⟩—C(O)—Cl | 82% | Yellow |

TABLE 3-continued

| Examples | Compounds | Yield | Color |
|---|---|---|---|
| 14 | (t)C₅H₁₁—⟨phenyl, C₅H₁₁(t)⟩—OCH₂CH₂CH₂C(O)NH—⟨phenyl⟩—C(O)—Cl | 85% | " |
| 15 | (t)C₅H₁₁—⟨phenyl, C₅H₁₁(t)⟩—OCH—C(O)NH—⟨phenyl⟩—C(O)—Cl | 83% | " |
| 16 | C₈H₁₇—⟨phenyl⟩—OCH₂CH₂CH₂C(O)NH—⟨phenyl⟩—CCl(O) | 80% | " |
| 17 | (t)C₅H₁₁—⟨phenyl⟩—OCH₂C(O)NH—⟨phenyl⟩—CCl(O) | 80% | " |
| 18 | (t)C₅H₁₁—⟨phenyl, C₅H₁₁(t)⟩—OCH₂CH₂CH₂C(O)NHCH₂CH₂C(O)Cl | 85% | " |

EXAMPLE 19

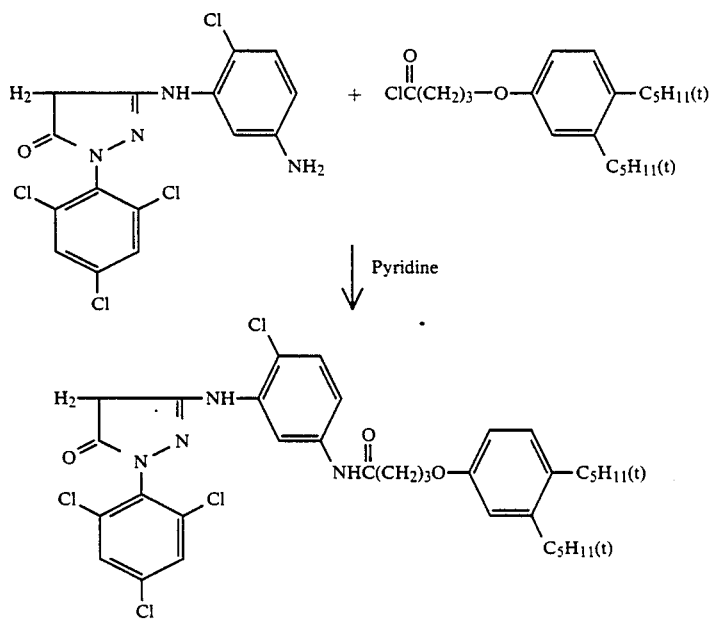

To a solution of 40 g of 1-(2,4,6-trichlorophenyl)-3-(5-amino-2-chloroanilino)-5-pyrazolone as a pyrazolone derivative in 300 ml of pyridine is added 38 g of 3-(2,4-di-test-phenylphenoxy)butylyl chloride synthesized in Example 2 as a ballasting group and the reaction is carried out with agitation at 30°–40° C. for 12 to 18 hours.

200 ml of n-hexane is added to the reaction product and the pyridine salt is filtered out, the solvent is distilled off under reduced pressure, and the residue is washed with methanol to obtain 62 g of white crystal (Yield 85 to 90%;

m.p. 230° to 233° C.).

IR: C=O (1695 cm$^{-1}$), NH(3400 cm$^{-1}$), CH(2960 cm$^{-1}$) NMR(CDCl$_3$ - DMSO - d$_6$ ): NH(9.7, 8.3, 8.1 ppm), CH$_2$(4.0 ppm)

Various conventional color-forming couplers prepared by the method of Example 19 are shown in Table 4.

TABLE 4
| Examples | Conventional color-forming couplers |
|---|---|
| 19 | 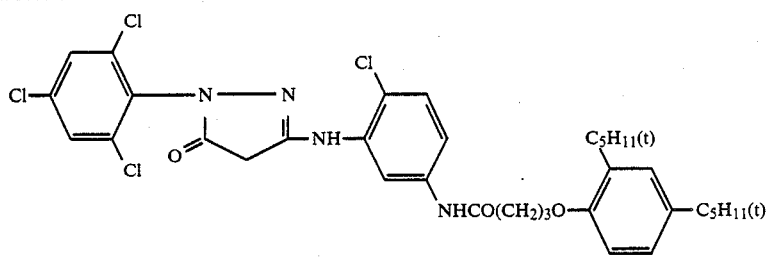 |
| 20 | 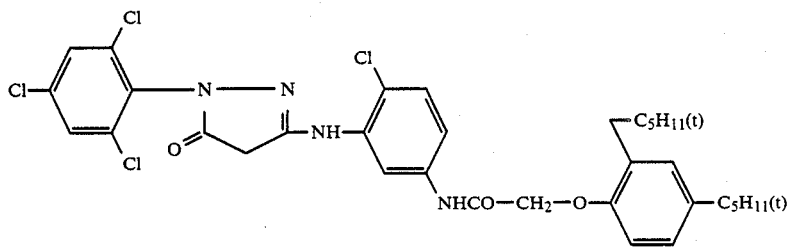 |
| 21 | 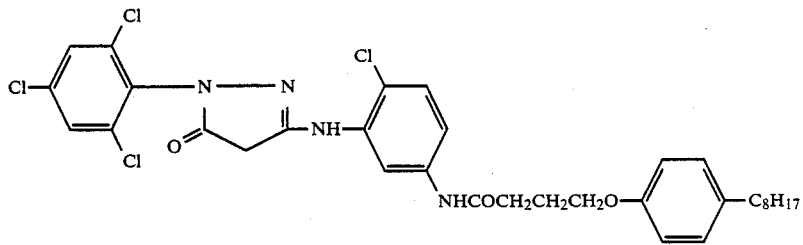 |
| 22 | 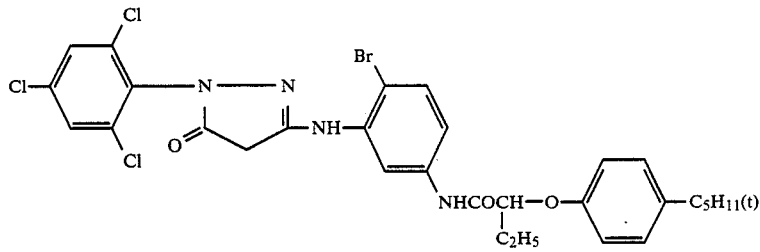 |
| 23 | 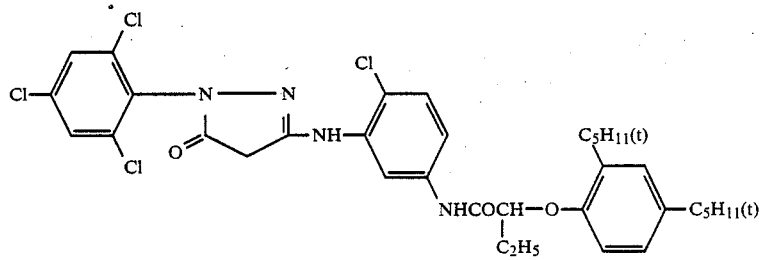 |
| 24 | 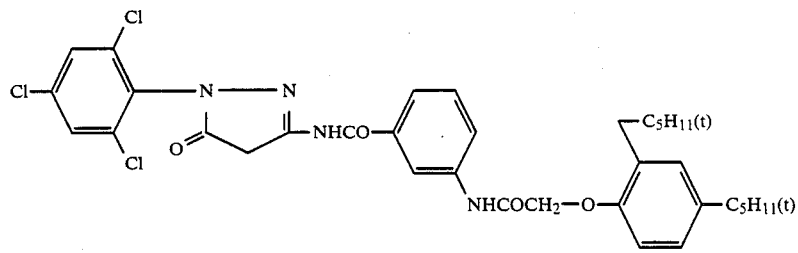 |

TABLE 4-continued

| Examples | Conventional color-forming couplers |
|---|---|
| 25 | 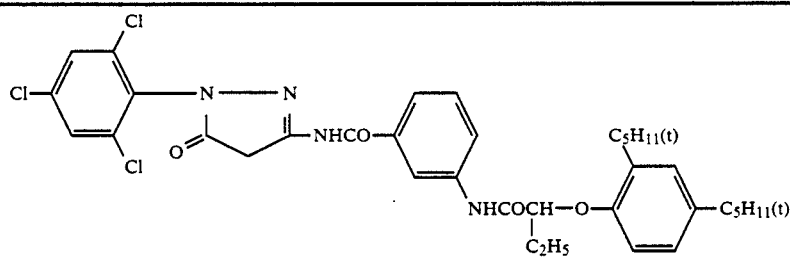 |
| 26 | 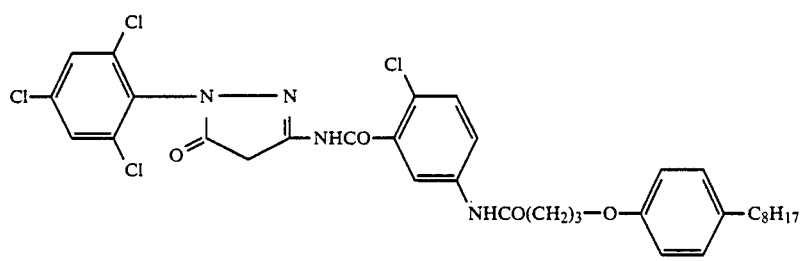 |
| 27 | 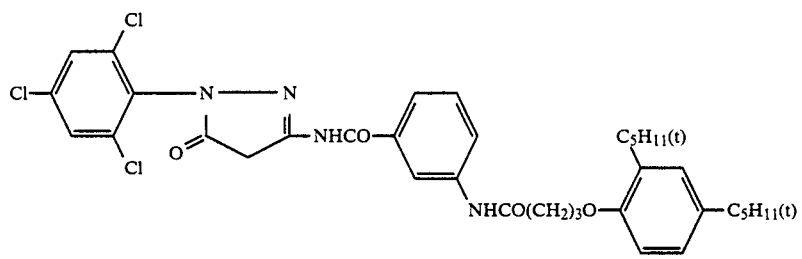 |

EXAMPLE 28-36

These examples illuminates the preparation of the color-forming coupler according to this invention wherein A denotes —$R^1$—COOH— in which $R^1$ represents $C_1$-$C_8$ alkylene or benzyl.

EXAMPLE 28

To a solution of 40 g of 1-(2,4, 6-trichlorophenyl)-3 (5-amino-2-chloroanilino)-5-pyrazolone as a pyrazolone derivative in 300 ml of pyridine is added 45 g of the ballasting group synthesized in Example 9 shown in Table 3 and the reaction is carried out with agitation at 80°–120° C. for 8–12 hours.

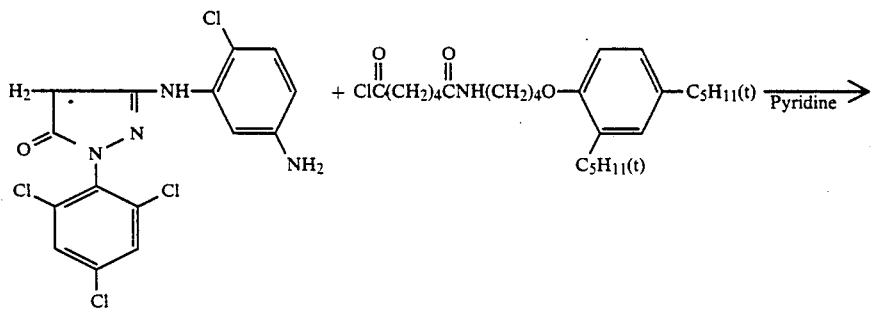

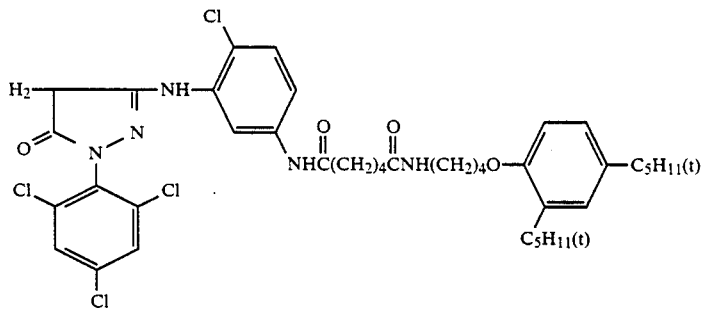

200 ml of n-hexane is added to the reaction product and the pyridine salt formed is filtered off, the solvent is distilled off under reduced pressure, and the residue is wished with tetrahydrofurane and methanol to obtain the titled coupler (yield 85%;
m.p. 118° to 120° C.).
IR: C=O (1685 cm$^{-1}$), NH(3410 cm$^{-1}$), CH(1960 cm$^{-1}$)
NMR(CDCl$_3$): NH(9.6, 8.6, 8.2 ppm), CH$_2$(3.9 ppm)

EXAMPLE 29 the reaction is carried out with agitation at 60°–80° C. for 12–15 hours.

After the reaction is completed 200ml of n-hexane is added to the reaction product and the pyridine salt formed is filtered off, the solvent is distilled off under reduced pressure, and the residue is washed with tetrahydrofurane and n - hexane to obtain the titled coupler (yield 80%; m. p. 136° to 139° C.).
IR: C=O(1700 cm$^{-1}$), NH(3410 cm$^{-1}$), CH(2980 cm$^{-1}$)
NMR(CDCl$_3$): NH(9.3, 8.2, 7.9 ppm), CH$_2$(3.8 ppm)

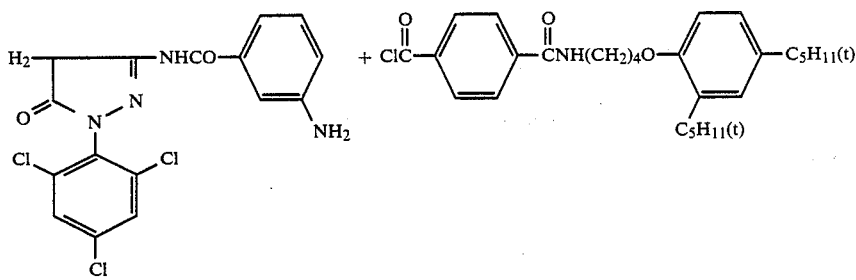

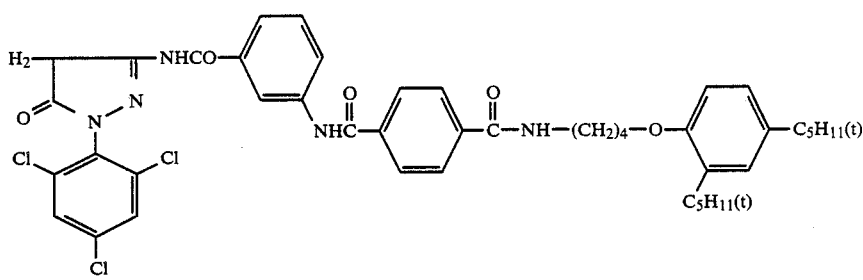

To a solution of 50 g of 1-(2,4,6-trichlorophenyl)-3-(3-aminobenzamide)-5-pyrazolone as a pyrazolone derivative in 300 ml of pyridine is added 42 g of the ballast group synthesized in Example 8 shown in Table 3 and Various color-forming couplers of this invention are shown in Table 5.

TABLE 5

| Examples | Magenta color-forming couplers |
|---|---|
| 30 | 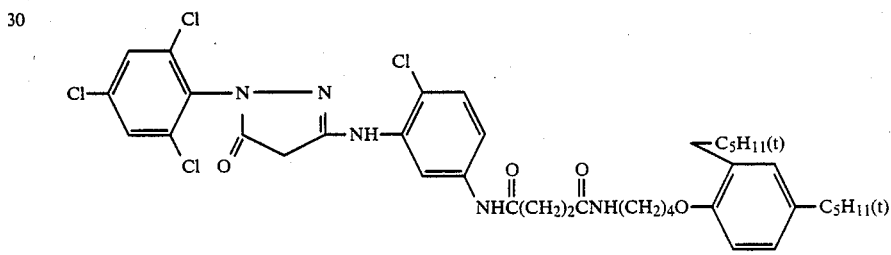 |
| 31 | 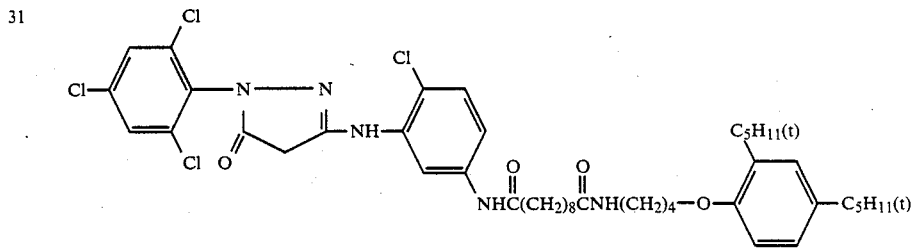 |

TABLE 5-continued
Examples  Magenta color-forming couplers
32
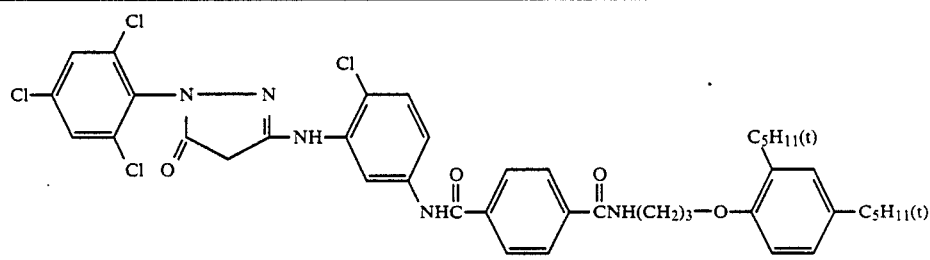
33
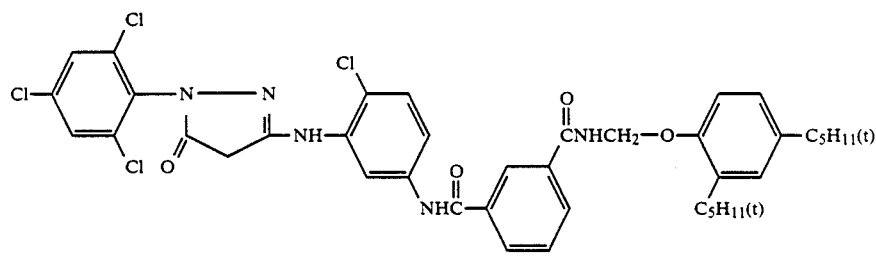
34
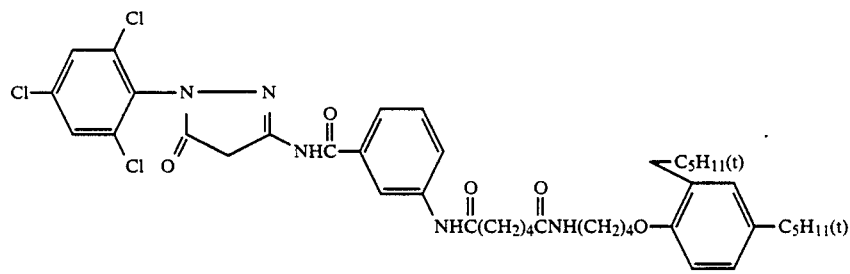
35
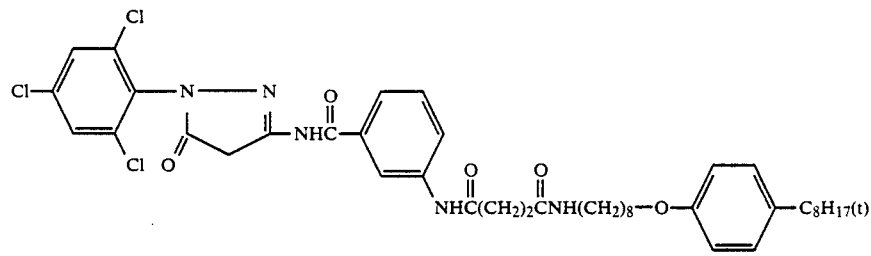
36
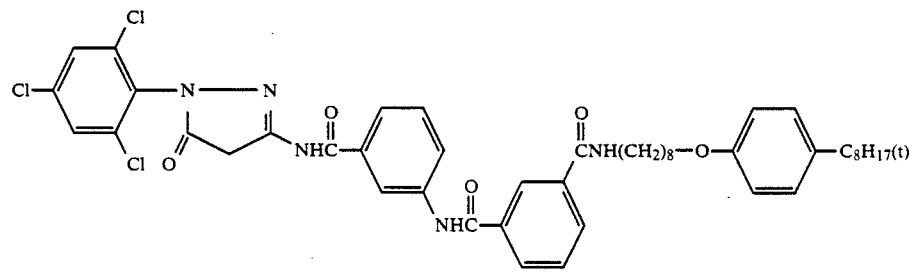
EXAMPLE 37-45
These examples illustrate the preparation of the color-forming coupler according to this invention wherein A denotes $-(R^2)_q-$NHCO$-$ in which $R^2$ represents $C_1-C_4$ alkylene or benzyl and q is 1, 2 or 3.
EXAMPLE 37

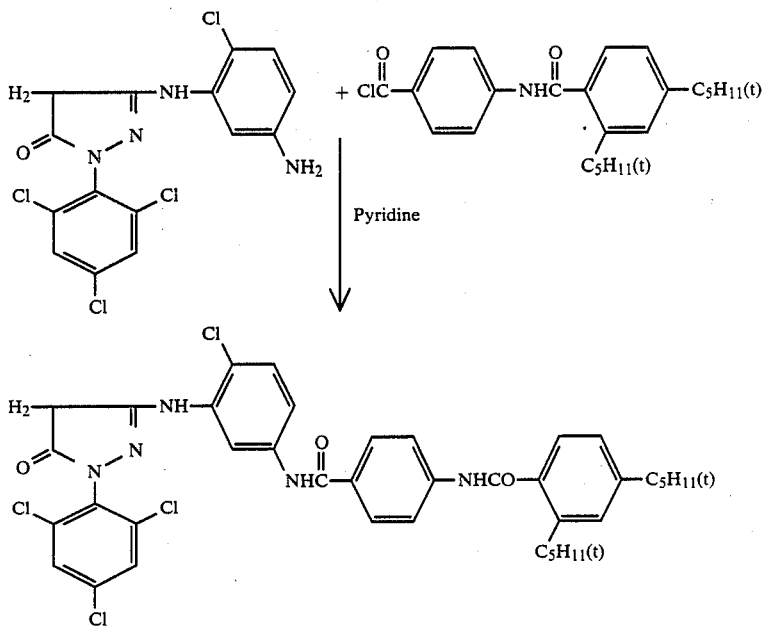

In 300 ml of pyridine 40 g of 1-(2,4,6-trichlorophenyl)-3-(5-amino-2-chloroanilino)-5-pyrazolone is reacted with 42 g of (2,4-di-tert-phenylphenoxy) acetyl-(p-benzoylchloride) amide synthesized in Example 13 at 50° to 80° C. for 12 to 15 hours.

After the reaction is completed, 200 ml of n - hexane is added to the reaction product and the pyridine salt is filtered off, the solvent is distilled off under reduced pressure, and the residue is washed with tetrahydrofurane and n - hexane to obtain the titled coupler (yield 70–85%;

m. p. 183°–183.5 ° C.).

IR: C=O(1693 cm$^{-1}$), NH(3400 cm$^{-1}$), CH(2970 cm$^{-1}$)

NMR(CDCl$_3$- DMSO - d$_6$): NH(9.5, 8.5, 8.1 ppm), CH$_2$(4.2 ppm)

Various color-forming couplers of this invention are shown in Table 6.

TABLE 6

| Examples | Magenta color-forming couplers |
|---|---|
| 38 | 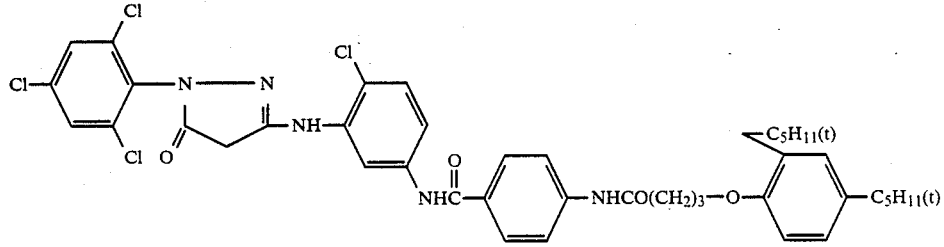 |
| 39 | 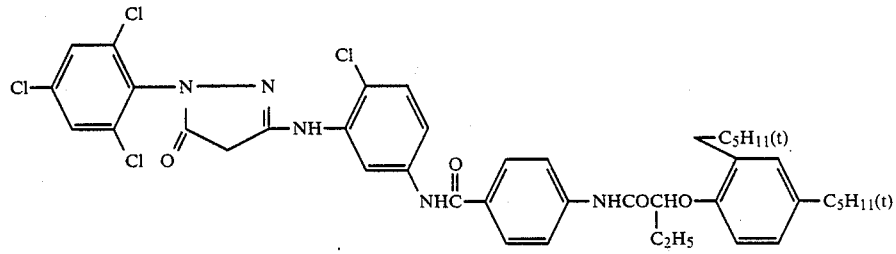 |

TABLE 6-continued
| Examples | Magenta color-forming couplers |
|---|---|
| 40 | 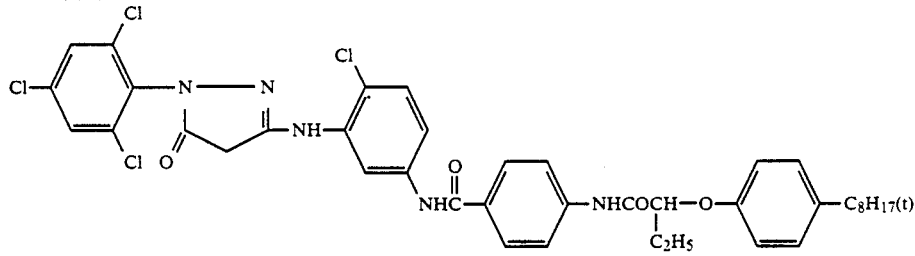 |
| 41 | 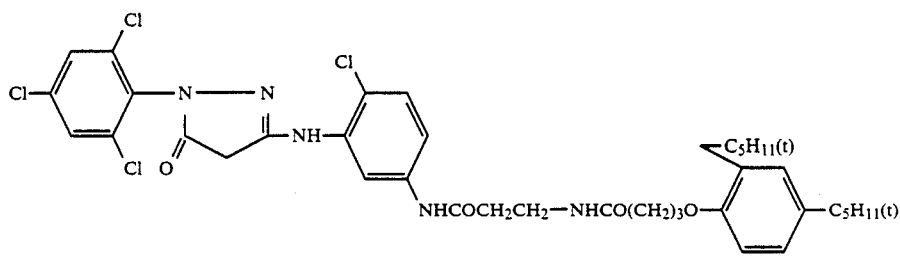 |
| 42 | 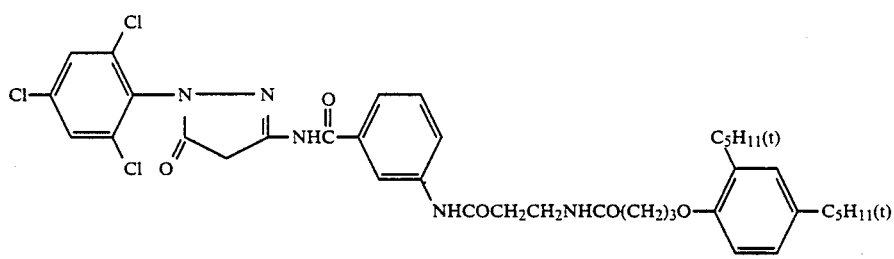 |
| 43 | 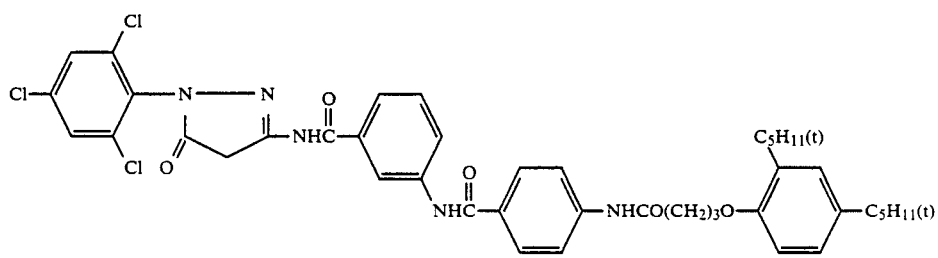 |
| 44 | 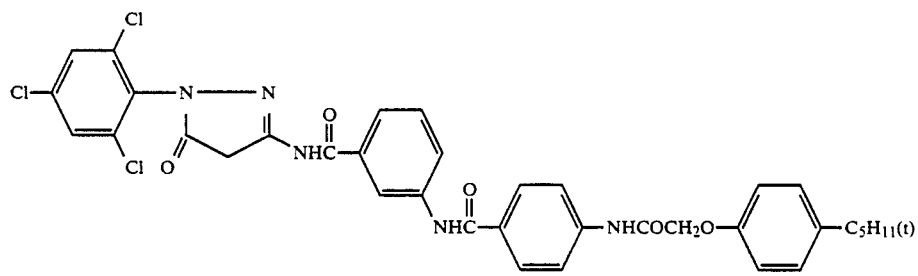 |
| 45 | 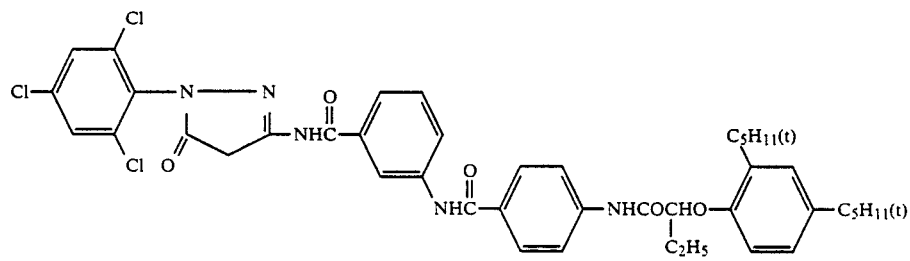 |
The green-sensitive couplers of the present invention together with the conventional red- and blue-sensitive couplers may be used in preparing the color photographic silver halide photosensitive materials. The redand blue-sensitive couplers which may be used in the photosensitive materials are those described in U.S. Pat. Nos. 3,265,506, 3,408,194 and GBP No. 521,550, and shown in Table 7 and 8, respectively.
TABLE 7
Red-sensitive couplers
C-1
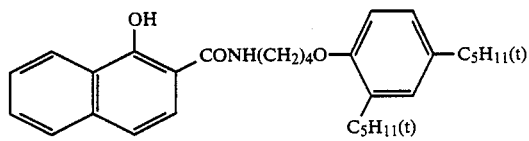
C-2
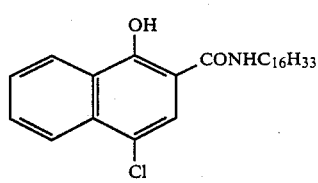
C-3
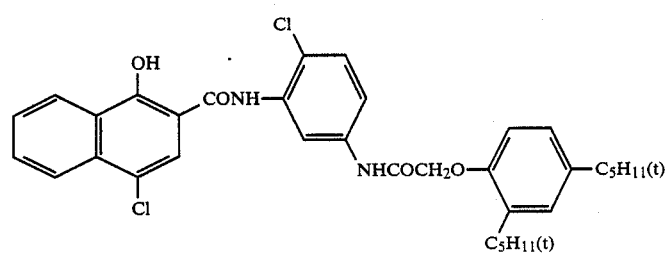
C-4
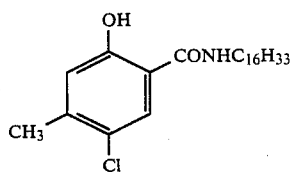
C-5
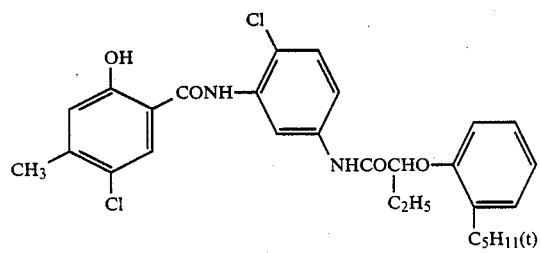
C-6
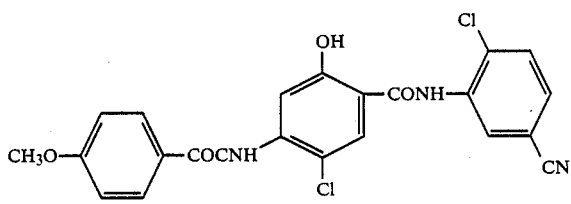

TABLE 8

Blue-sensitive couplers

Y-1: [structure with Cl-phenyl, CH3-C(CH3)2-COCHCl-CONH-, NHCOCH(C2H5)O-phenyl-C5H11(t), C5H11(t)]

Y-2: [structure with Cl-phenyl, CH3-C(CH3)2-COCHCl-CONH-, NHCO(CH2)3-O-phenyl-C5H11(t), C5H11(t)]

Y-3: [structure with Cl-phenyl, CH3-C(CH3)2-COCH2CONH-, COOCH(C2H5)COOC12H25]

Y-4: [structure with CH3-C(CH3)2-COCHCONH-phenyl-COOC12H25, hydantoin ring with C2H5O and N-CH2-phenyl]

Y-5: [structure with Cl-phenyl, CH3-C(CH3)2-COCHCl-CONH-, NHSO2C16H33]

Y-6: [structure with C16H33O-phenyl-CCHCNH-, Cl-phenyl-SO2N(CH3)2, imidazoline with CONH-phenyl]

Prior to preparing the emulsion for color photographic photosensitive materials the above-mentioned red- and blue-sensitive couplers together with the green-sensitive of the present invention are resolved and dispersed in a mixed solvent of the high boiling solvents and low boiling solvents. In the present invention, the diesters of phthalic acids shown in Table 9 are used as the high boiling solvents and ethylacetate or chloroform as the low boiling solvents. Then, the solution is poured into the gelatin emulsion containing various additives, dispersed by using a high speed rotary mixer, and the resulting emulsion is added to a silver halide emulsion to prepare a silver halide photographic emulsion. In the present invention, about 0.05 to 0.2 mole of the green-sensitive couplers is used per 1 mole of silver halide contained in silver halide emulsion.

TABLE 9

(High-boiling solvents)

(HBS-1) Phthalate with two $COOC_3H_7$ groups (HBS-2) Benzene with $COOC_4H_7$ and $COOCH_2CHC_4H_9$ ($C_2H_5$ branch)

(HBS-3) Phthalate with two $COOCH_2$-cyclohexyl groups (HBS-4) Phthalate with two $COOC_{10}H_{21}$ groups (HBS-5) Isophthalate with two $COOC_4H_9$ groups (HBS-6) Isophthalate with two $COOC_8H_{17}$ groups (HBS-7) $O=P(-OC_4H_9)_3$ (HBS-8) $C=P(-OC_6H_{13})_3$ (HBS-9) $O=P(-OCH_2-\text{phenyl})_3$ (HBS-10) $O=P(-OCH_2CHC_4H_9)_3$ with $C_2H_5$ branch (HBS-11) Phenol with $C_5H_{11}(t)$ ortho and $C_5H_{11}(t)$ para (HBS-12) Phenol with $C_7H_{19}$ ortho and $C_5H_{11}$ para (HBS-13) $HO$-phenyl-$C_{12}H_{25}$ (HBS-14) Phenol with $C_4H_9(t)$, $C_4H_9(t)$, and $C_8H_{17}$ (HBS-15) Phenol with $C_8H_{17}(t)$ and $C_6H_{13}(t)$ (HBS-16) Phenol with $C_6H_{13}$ and $C_6H_{13}$ The sensitizers suitable for use in preparing of the green-sensitive emulsions of the present invention in consideration of pH, pAg and characteristics of the photographic emulsions are SD - 4, SD - 5 or SD - 9 described in "Dye for Photo" [Japan Photosensitive Dyestuff Laborotory (1972)]. The added amount of the sensitizer as 0.1% methanol solution is about 0.1 to 2 ml per 1 g of $AgNO_3$.

The UV absorbers suitable for use in the present invention are show in Table 10 below. In the practice according to the present invention, about 0.5 to 1.5 ml of UV - 4 per 500 g of the photographic emulsion is used.

TABLE 10

(UV-absorbers)

UV-1: Benzotriazole linked to phenol with $OH$ and $C_4H_9(t)$

TABLE 10-continued
(UV-absorbers)

UV-2: benzotriazole with OH and two C4H9(sec) groups on phenol ring

UV-3: benzotriazole with OH, C4H9(t) and CH3 groups on phenol ring

UV-4: benzotriazole with OH and two C5H11(t) groups on phenol ring

UV-5: $(C_2H_5)_2NCH=CH-CH=C(COOC_{12}H_{25})(C_6H_5)$

UV-6: $CH_3-C_6H_4-CH=C(CN)(COOC_{16}H_{33})$

The stabilizers used in the practice of the present invention are selected from 1-phenylmercaptotetrazole, mercaptobenzimidazole and the mixture thereof, and the added amount is about 0.05 to 2 ml/lg of $AgNO_3$.

And, is may be used in the practice of the present invention dodecylamineacetate or sodium dodecylbenzene sulfonate as a surfactants having good effects on the surface tension of the emulsion, uniform dispersion of the couplers and stabilization of the colloidal emulsion. The added amount of the surfactants as a form of 5% methanol solution is about 0.1 to 0.5 ml/lg of $AgNO_3$.

The couplers and additives described above will be used to prepare the silver halide emulsion of the Example 41 to 48 below. In the Example 46 to 48, the mixed emulsion of AgBr and AgCl having a particle size of about 0.3 to 0.8 um is used and the mixed emulsion is prepared by using a conventional method.

EXAMPLE 46

This example illustrates the preparation of the emulsion coating containing the conventional coupler synthesized in Example 23.

1. Physical Aging

| Solution A: | Distilled water | 1.2 l |
|---|---|---|
| | Gelatin | 15 g |
| | KBr | 41 g |
| | NaCl | 12 g |
| | Citric acid | 1.5 g |
| Solution B: | Distilled water | 550 ml |
| | AgNO3 | 30 g |
| Solution C: | Distilled water | 320 ml |
| | Gelatin | 27 g |
| | NaCl | 18 g |
| Solution D: | Distilled water | 550 ml |
| | AgNO3 | 70 g |
| Solution E: | Distilled water | 240 ml |
| | Gelatin | 60 g |

To Solution A maintained at a temperature of 60° to 80° C. is added Solution B maintained at a temperature of 55° to 60° C. After twenty seconds, Solution C is added to the mixture of A and B. And then, after two minutes, Solution D and E are added simultaneously to the admix and the resultant mixture is aged for 30 minutes to obtain an emlusion having a diameter thereof is 0.3 to 0.8 μm.

2. Washing

The emulsion obtained in step 1 is washed with water maintained at a temperature of not more than 10° C. and stirred slowly to make conductivity of the emulsion about 700 to 100 μΩ/cm.

3. Chemical Aging

After complete solving of the emulsion at a temperature of not more than 40° C., the solution of 1% methanol in 1 ml of benzotriazole is added per 10 g of $AgNO_3$, 0.5 ml of aqueous solution of 10% KBr is added, and 1 ml of sodium sulfite as a sensitizer is added thereto per 10 g of $AgNO_3$. And then the admixture is stirred for about an hour and 5 ml of sensitizer of SD -4 or SD -5 is added per 10 g of $AgNO_3$ to complete the emulsion preparation.

4. To a solution of 18 g of coupler synthesized in Example 23 in 20 ml of tritolyl phosphate as a high boiling point solvent and 100 to 150 ml of ethylacetate chloroform as a low boiling point solvent are added 2 to 3 g of dodecylamine acetate or sodium dodecylbenzenesulfonate as a stabilizer, and 4 to 5 g of UV - 4 as a UV absorber shown in Table 10. Then, the reaction mixture is emulsified in a solution of 300 g of gelatin in 300 ml of water and the resulting admixture is mixed with the emulsion obtained step 3 to prepare the emulsion coating.

The emulsion coating prepared above is coated with a thickness of about 0.5 to 2 μm on the RC support. After being dried, the photographic characteristics curves are drawn in FIG. 1.

Fog density and maximun color-forming density are shown in Table 11.

EXAMPLE 47

This example illustrates the preparation of the emulsion coating containing the coupler of the present invention synthesized in Example 35.

The emulsion coating is prepared by a process similar to that used for Example 46 but in which a equivalent amount of the coupler of the present invention synthesized in Example 35 is used in place of the coupler synthesized in Example 23.

The results obtained are shown in FIG. 1 and Table 11.

EXAMPLE 48

This example illustrates the preparation of various emulsion coatings containing 27 couplers synthesized in Example 19 to Example 45, respectively, are prepared by the methods similar to those described in Example 46 and Example 47 above.

These emulsion coatings are coated on RC support such that coated amount of Ag will be 0.3 to 0.8 g/m² and dried to obtain stable samples to be used in developing step.

Samples of these coatings are wedge-exposed by a conventional method and processed by developing each of them under conditions of Fuji CN-20 Processing.

The processed samples are then exposed by using a photosensitometer to measure sensitivity and maximum color-forming density of the samples with Mcbeth TR-754 density tester. The results obtained are given in Table 11 below.

Then, the samples are processed for 8 hours and 48 hours, respectively, under conditions of 538 Lux of illumination, 60° C. of temperature(for 8 hours) and 90° C. of temperature (for 48 hours), and 50% of relative humidity. The results are shown in FIG. 2 and FIG. 3, respectively.

FIG. 4 attached shows each absorption spectrum as to the samples.

TABLE 11

| Color-forming couplers of Examples below | Basic fog density | Maximum color-forming density | Fog density after color -fading test | ΔDf |
| --- | --- | --- | --- | --- |
| 20 | 0.02 | 1.57 | 0.04 | 0.02 |
| 23 | 0.02 | 1.49 | 0.04 | 0.02 |
| 24 | 0.02 | 1.66 | 0.05 | 0.03 |
| 27 | 0.02 | 1.72 | 0.04 | 0.02 |
| 28 | 0.02 | 1.78 | 0.05 | 0.03 |
| 29 | 0.02 | 1.68 | 0.03 | 0.01 |
| 32 | 0.01 | 1.72 | 0.03 | 0.02 |
| 34 | 0.01 | 1.74 | 0.03 | 0.02 |
| 37 | 0.01 | 1.70 | 0.04 | 0.03 |
| 39 | 0.03 | 1.72 | 0.04 | 0.01 |
| 41 | 0.03 | 1.72 | 0.05 | 0.02 |
| 43 | 0.02 | 1.74 | 0.05 | 0.03 |
| 45 | 0.01 | 1.77 | 0.03 | 0.02 |

Notes:
1. Conventional color-forming couplers each prepared in Examples 20, 23, 24 and 27 are those described in U.S. Pat. Nos. 2,343,703, 3,615,506, 3,419,391, 4,374,253 and 4,010,035.
2. "ΔDf" means the difference between fog density after color-fading test and basic fog density.

As is apparent from Table 11, by using the magenta couplers of the present invention, not only excellent maximum color-forming density but also poor fog production and fog density after color-fading test can be obtained as compared with the conventional magenta couplers of Examples 20, 23, 24, and 27. Particularly, when the green-sensitive color-forming the photographic material, high color-forming density can be obtained (see FIG. 1).

What is claimed is:

1. A compound of the formula:

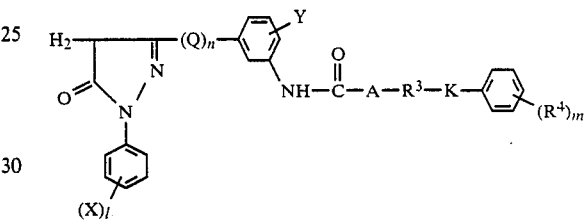

wherein X is halogen; l is 0, 1, 2 or 3; Y is hydrogen or halogen; Q is —NH— or —NHCO—; n is 1, 2 or 3; K is O, S or $SO_2$; A is —$R^1$—CO—NH— or —$(R^2)_q$-NHCO in which $R^1$ represents $C_1$-$C_8$ alkylene or phenylene, $R^2$ represents $C_1$-$C_4$ alkylene or phenylene and q is 1, 2 or 3; $R^3$ is $C_1$-$C_8$ alkylene; $R_1$-$C_8$ alkyl; and m is an integer of 0, 1 or 2, provided that a plurality of $R^4$ are the same or different each other when m is 2.

* * * * *